United States Patent [19]

Hayashi et al.

[11] Patent Number: 5,485,231
[45] Date of Patent: Jan. 16, 1996

[54] APPARATUS FOR VISUAL ACUITY TEST HAVING AN ADJUSTABLE MIRROR

[75] Inventors: Akihiro Hayashi, Toyokawa; Kazuhiro Yoshimura, Toyohashi; Yasuhisa Murakami, Anjo; Yasumi Hikosaka, Gamagori, all of Japan

[73] Assignee: Nidek Co., Ltd., Japan

[21] Appl. No.: 380,001

[22] Filed: Jan. 27, 1995

[30] Foreign Application Priority Data

Jan. 31, 1994 [JP] Japan .................................. 6-029074
Feb. 28, 1994 [JP] Japan .................................. 6-055191

[51] Int. Cl.⁶ .................................................. A61B 3/02
[52] U.S. Cl. ............................................ 351/243; 351/239
[58] Field of Search .................................. 351/243, 239, 351/245, 244, 222, 237, 227

[56] References Cited

U.S. PATENT DOCUMENTS 4,403,842  9/1983  Aulhorn et al. ..................... 351/243

FOREIGN PATENT DOCUMENTS

63-28613  4/1984  Japan .

Primary Examiner—William L. Sikes
Assistant Examiner—Hung Xuan Dang
Attorney, Agent, or Firm—Parkhurst, Wendel & Rossi

[57] ABSTRACT

An apparatus for visual acuity test of an examinee's eye comprises test chart presenting device for changing and presenting test chart to the examinee's eye, a switch for designating test chart to be presented by the test chart presenting means, a light delivery optical system for delivering luminous flux of test chart from the test chart presenting means to the examinee's eye, the light delivery optical system comprising a concave mirror for making the luminous flux of test chart optically from 4 m ahead of the examinee to infinit and a first reflection mirror for reflecting the luminous flux reflected the concave mirror to the examinee's eye, and reflecting angle adjusting device for adjusting reflection angle of the reflection mirror so as to fit to a height of the examinee's eye, a housing for internally mounting the test chart presenting means and the light delivery optical system, the housing having an aperture to allow the luminous flux of test chart pass therethrough and the aperture being provided with a filter on which reflection reducing coating is coated.

9 Claims, 14 Drawing Sheets

APPARATUS FOR VISUAL ACUITY TEST HAVING AN ADJUSTABLE MIRROR

BACKGROUND OF THE INVENTION

1. Field of the Invention

The present invention relates to an apparatus for visual acuity test, capable of examination of visual acuity of an examinee's eye in a test space reduction type.

2. Description of Related Art

Visual acuity test generally needs a predetermined test distance between a test apparatus and an examinee's eye to be examined. There have been so far proposed visual acuity test apparatuses of space reduction type, wherein an eye test distance needed is optically retained by use of mirrors and the like, without arranging visual test charts or optotypes in a straight line with respect to an eye of an examinee.

This sort of apparatus has a relatively small mirror for reflecting luminous flux of test chart to the examinee's eye, so that the examinee may view the test chart disposed within the apparatus via the mirror.

The above apparatus utilizing mirror reflection to present test chart to an examinee, however, has poor acceptance with respect to variation in the location of the examinee's eye, therefore causing a demerit of obliging an examiner whose sitting height is short to take an unnatural pose.

SUMMARY OF THE INVENTION

The present invention has been made in view of the above circumstances and has an object to overcome the above problems and to provide an apparatus for visual acuity test capable of testing an examinee's eye in a proper state regardless of physical condition of the examinee.

Another object of the present invention is providing a visual acuity test apparatus which has a simple construction as far as possible and can examine the exact visual acuity of the examinee's eye.

Additional objects and advantages of the invention will be set forth in part in the description which follows and in part will be obvious from the description, or may be learned by practice of the invention. The objects and advantages of the invention may be realized and attained by means of the instrumentalities and combinations particularly pointed out in the appended claims.

To achieve the objects and in accordance with the purpose of the invention, as embodied and broadly described herein, an apparatus for visual acuity test of this invention comprises means for changing and presenting test chart to the examinee's eye, a switch for designating test chart to be presented by the test chart presenting means, a light delivery optical system for delivering luminous flux of test chart from the test chart presenting means to the examinee's eye, the light delivery optical system comprising a concave mirror for making the luminous flux of test chart optically from 4 m ahead of the examinee to infinite and a first reflection mirror for reflecting the luminous flux reflected the concave mirror to the examinee's eye, and means for adjusting reflection angle of the reflection mirror so as to fit to a height of the examinee's eye, a housing for internally mounting the test chart presenting means and the light delivery optical system, the housing having an aperture to allow the luminous flux of test chart pass therethrough and the aperture being provided with a filter on which reflection reducing coating is coated.

In a second aspect of the present invention, an apparatus for visual acuity test of an examinee's eye comprises means for changing and presenting test chart to the examinee's eye, a switch for designating test chart to be presented by the test chart presenting means, a light delivery optical system for delivering luminous flux of test chart from the test chart presenting means to the examinee's eye, the light delivery optical system comprising a concave mirror for making the luminous flux of test chart optically from 4 m ahead of the examinee to infinit and a first reflection mirror for reflecting the luminous flux reflected the concave mirror to the examinee's eye, means for adjusting reflection angle of the first reflection mirror, means for detecting a height of the examinee's eye, and means for controlling the mirror angle adjusting means based on results detected by the height detecting means.

According to the present invention, eye test can be carried out in a proper state regardless of physical condition of the examinee.

The apparatus of the present invention is space reducing type and convenient, and can improve an operational deal itself.

BRIEF DESCRIPTION OF THE DRAWINGS

The accompanying drawings, which are incorporated in and constitute a part of this specification illustrate an embodiment of the invention and, together with the description, serve to explain the objects, advantages and principles of the invention. In the drawings.

DETAILED DESCRIPTION OF THE PREFERRED EMBODIMENTS

A detailed description of a first preferred embodiment of an apparatus for visual acuity test embodying the present invention will now be given referring to the accompanying drawings.

The present embodiment shows the construction of the apparatus separately into a body of visual acuity test apparatus and a remote control unit.

(Body of apparatus for visual acuity test)

Figure 1:
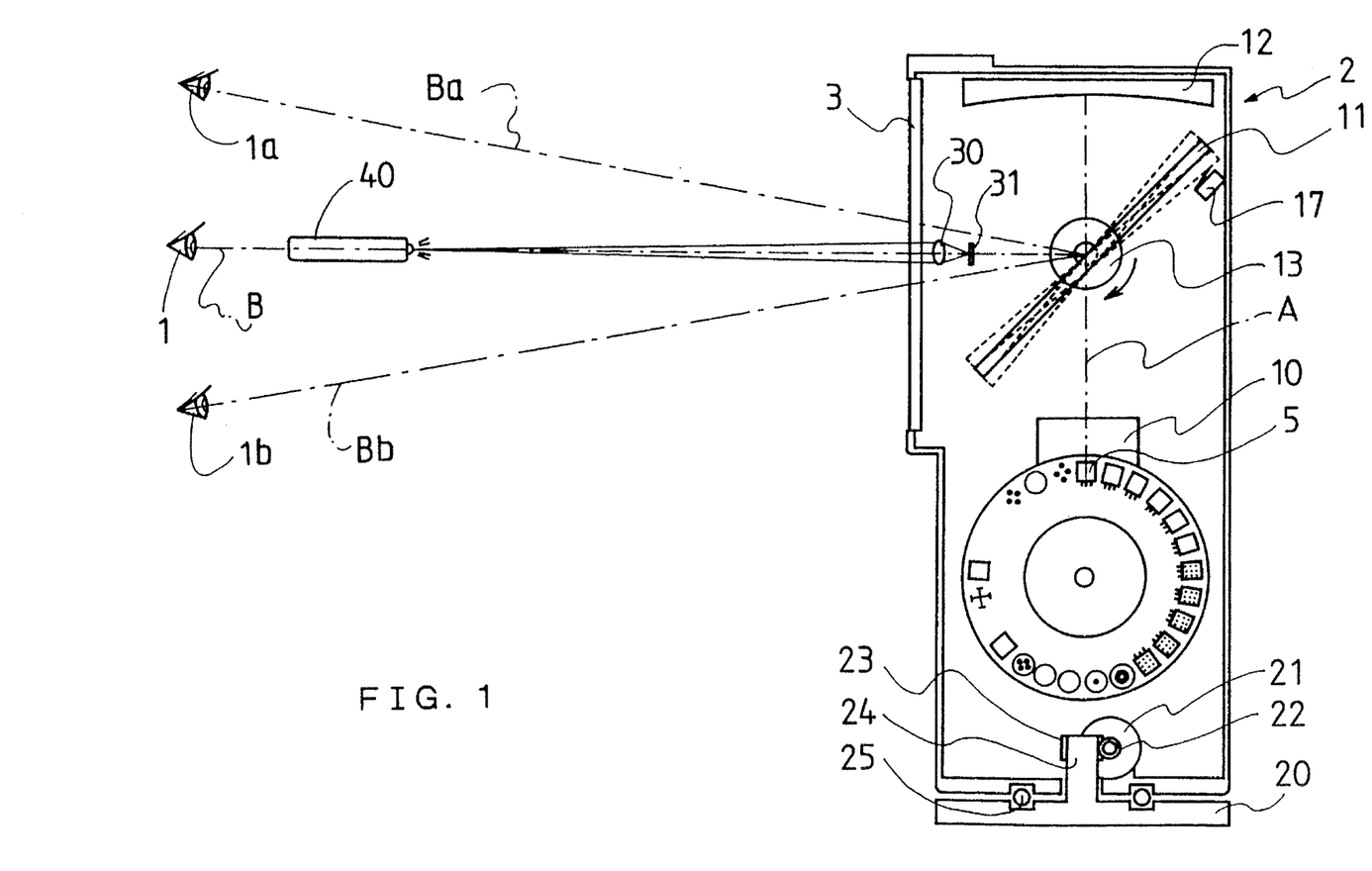
FIG. 1 is a schematic perspective right side view of an apparatus in a first embodiment in accordance with the present invention.
Figure 2:
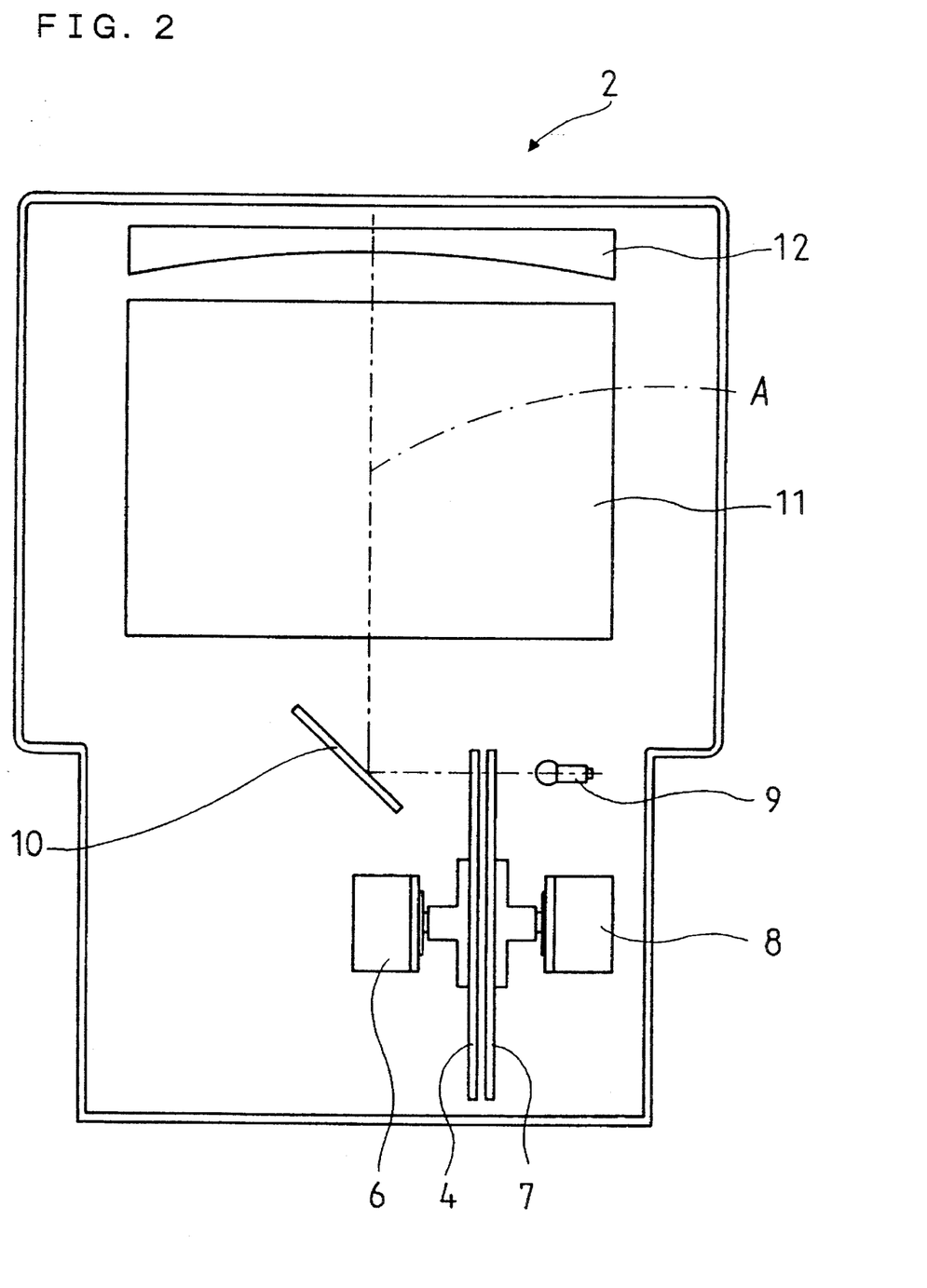
FIG. 2 is a schematic perspective front view of the apparatus of the first embodiment.

In FIG. 1, numeral 1 is an eye of an examinee and numeral 2 is a body of an apparatus for visual acuity test to present a test chart to the examinee's eye 1. The body 2 of the apparatus has a window 3 with a glass plate on which a reflection reducing coating is provided and through which the examinee looks at a test chart. It is be more preferable to arrange a filter instead of the glass plate in the window 3. The inside of the body 2 is painted in black color so that the examinee can hardly see the interior structure of the body 2.

The body 2 is internally provided with a circular disc plate 4 made of a glass material and the like on which test charts 5 are provided in a circle by chrome evaporation and disc surface of which is arranged parallel to the visual line of the examinee's eye 1, a motor 6 for driving the disc plate 4 to rotate thereby to change a test chart 5 to be presented to the examinee, a mask plate 7 for partially masking the test charts on the disc plate 4 and a motor 8 for driving the mask plate 7 to rotate to cover test chart with desired and necessary mask.

Inside of the body 2, also provided are an illumination lamp 9 to illuminate a test chart, a mirror 10, a beam splitter 11 and a concave mirror 12. The test chart 5 is arranged at the focus distance of the concave mirror 12. It is possible to put an optical distance between the test chart and the examinee's eye in a finit distance, for instance 4 or more meters (provided by the ISO; International Standard Organization). Luminous flux of the test chart 5 illuminated by the illumination lamp 9 is upwardly reflected by the mirror 10, passes along an optical path indicated by "A" in the figures and through the beam splitter 11 to the concave mirror 12. The luminous flux is then reflected by the concave mirror 12 and, succeedingly, by the beam splitter 11 toward the examinee's eye 1 along an optical path indicated by B in the figures.

The beam splitter 11 is so constructed to change its inclination angle in order to shift up or down a reflecting orientation of luminous flux of test chart as shown by dotted lines in FIG. 1. Numeral 13 is a motor for changing the inclination angle of the beam splitter 11, which is mounted inside the body 2 and on which a support shaft 14 to support the beam splitter 11 is fixed. The beam splitter 11 is at the same time supported by a support shaft 15 which is coaxial with the support shaft 14 and is joined rotatably to the body 2 via a bearing 16. The inclination angle of the beam splitter 11, that is, its rotating angle is changed in accordance with rotation of the motor 13, so that an optical path indicated by B, along which a light beam of the test chart after reflected by the beam splitter 11 is projected to the eye 1, is shifted to an optical path indicated by Ba or Bb according to the position of the examinee's eye 1a or 1b. These eyes 1a and 1b show respectively a state where a height of the examinee's eye is different from that of the eye 1 based on each sitting height and so on.

Numeral 17 is a microswitch for detecting an initial position of an inclination angle of the beam splitter 11.

Upper portion of the body 2 of the visual acuity test apparatus is supported rotatably in a horizontal direction by a fixed base 20. Numeral 21 is a motor for rotating the upper portion of the body 2 in a horizontal direction and is provided with a wheel 22 on its rotary shaft. The fixed base 20 has a shaft 24 integrated thereon, the shaft 24 being coaxial with the optical path indicated by A and provided thereon with a worm wheel 23 which engages with the wheel 22. As the wheel 22 is rotated by the motor 21, accordingly, the upper portion of the body 2 is rotated in a horizontal direction with respect to the fixed base 20 via a thrust bearing 25, so that a reflection direction of luminous flux of the test chart by the beam splitter 11 is moved in lateral direction.

The body 2 of the apparatus is also provided with a system for detecting a position of the examinee's eye 1, constructed of a condenser lens 30 and a two-dimensional position detecting element 31. The condenser lens 30 serves to condense an infrared light emitted from an emitting portion of a remote control unit mentioned later on the two-dimensional position detecting element 31 to form an image of the emitting portion. This element 31 uses preferably semiconductor position detecting element which would be used in auto-focus cameras and the like. In such detecting system, a position of the emitting portion of the remote control unit in vertical and horizontal directions is detected based on a position of the image of the emitting portion formed on the two-dimensional position detecting element 31.

The detecting systems, each of which has a condenser lens 30 (30a) and two-dimensional position detecting element 31 (31a), are arranged symmetrically with respect to a center axis of the beam splitter 11, so that position detecting signal of the remote control unit can be transmitted to the detecting system from either right or left side of the examinee.

The body 2 comprises a transmitting portion and a receiving portion for communication of a signal to exchange a test chart, namely, a light receiving portion 32 which receives a signal from the remote control unit and a light emitting portion 33 which transmits an optical signal for confirmation to the remote control unit.

(Remote control unit)

Figure 4:
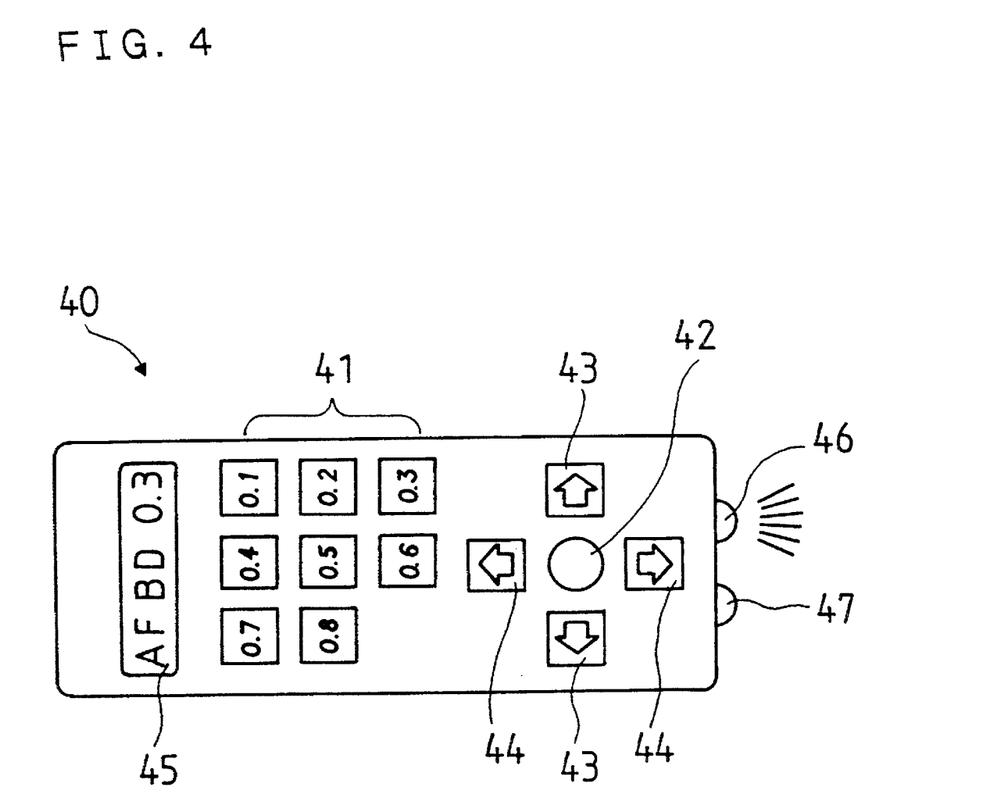
FIG. 4 is a schematic plane view of a remote control unit for changing a test chart to be presented to an examinee.

FIG. 4 shows an remote control unit 40 for exchanging a test chart to be presented to the examinee's eye. The remote control unit 40 is provided with a group of buttons 41 for selecting a test chart of visual acuity value requested, a button 42 to transmit an optical signal for detecting of a position of the examinee's eye, buttons 43, 44 in use for manual operations to drive the motor 13 or another motor 21 in order to change an optical path of test chart, a display portion 45 for displaying test charts presented in the body 2. In the rear side of the unit 40, are provided with an light emitting portion 46 to generate a pulse signal of infrared light and a light receiving portion 47 for receiving an optical signal emitted from the emitting portion 33 of the body 2.

Figure 5:
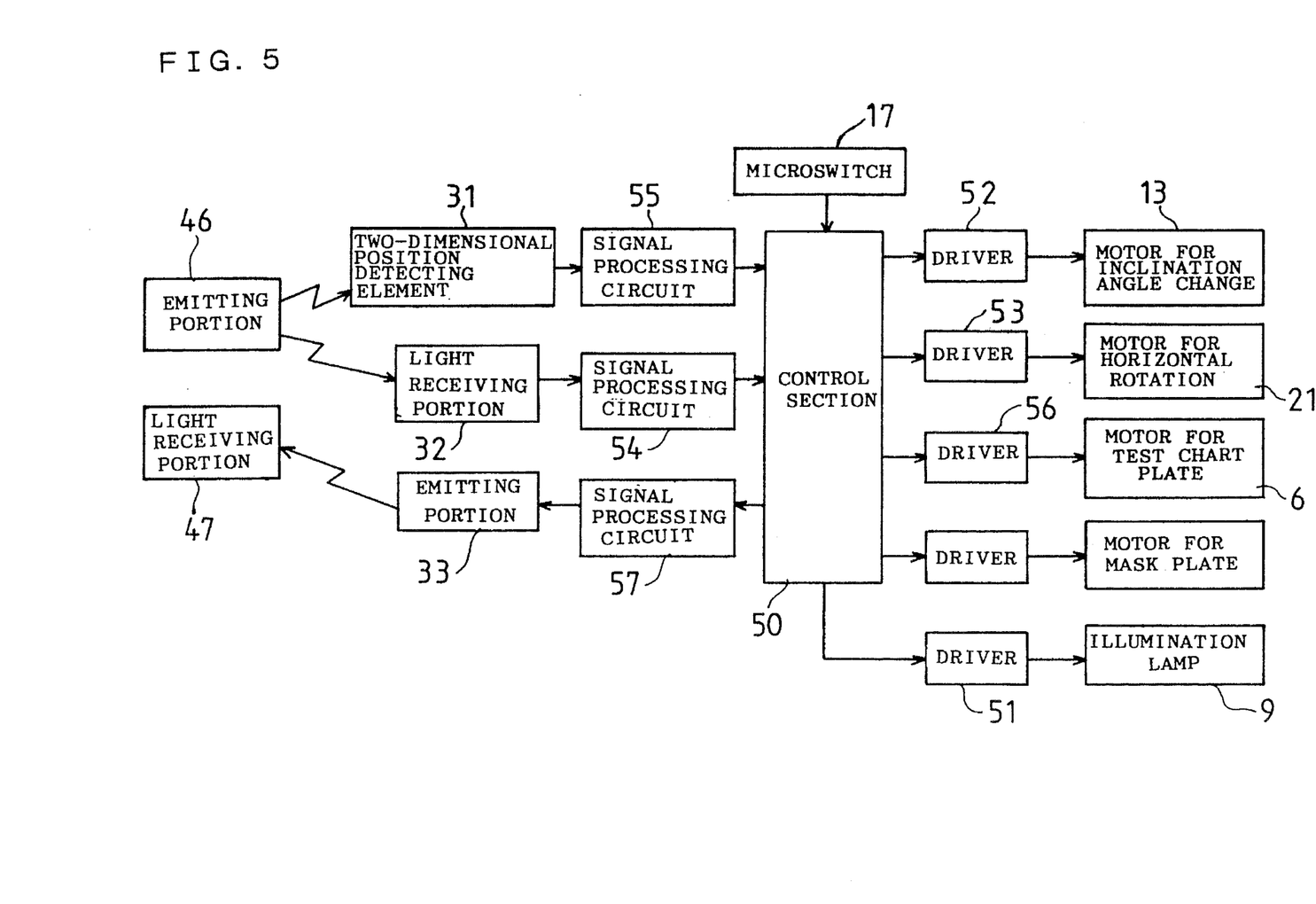
FIG. 5 is a block diagram of an electric system of the apparatus in the first embodiment.

Operation of the apparatus as constructed above will be described hereinafter with reference to a block diagram of an electric system of the apparatus shown in FIG. 5.

An examiner makes, first, the examinee take a predetermined position in front of the apparatus, then turns on a power switch not shown in the figure. Control section 50 of the body 2, after receiving the signal, turns on the illumination lamp 9 via a driver 51 and at the same time rotates the motor 13 for change of the inclination angle and the motor 21 for horizontal movement in a positive direction via drivers 52 and 53 respectively. In accordance with positive rotation of the motor 13, the beam splitter 11 rotates clockwise in FIG. 1. When the beam splitter 11 rotating comes in touch with the microswitch 17 in its upper back surface as shown by a doted line in FIG. 1, the microswitch 17 transmits electricity and the control section 50 detects an initial position. After that, the control section 50 rotates the motor 13 in a reverse direction until the optical path along which a light of a test chart passes comes into the optical path indicated by B which substantially fit to a standard height of an examinee's eye. Similarly, the body 2 is rotated in a horizontal direction by positive rotation of the motor 21 and an initial position is determined based on a signal of a microswitch not shown in the figure, then the motor 21 is rotated in reverse by a predetermined angle.

Figure 3:
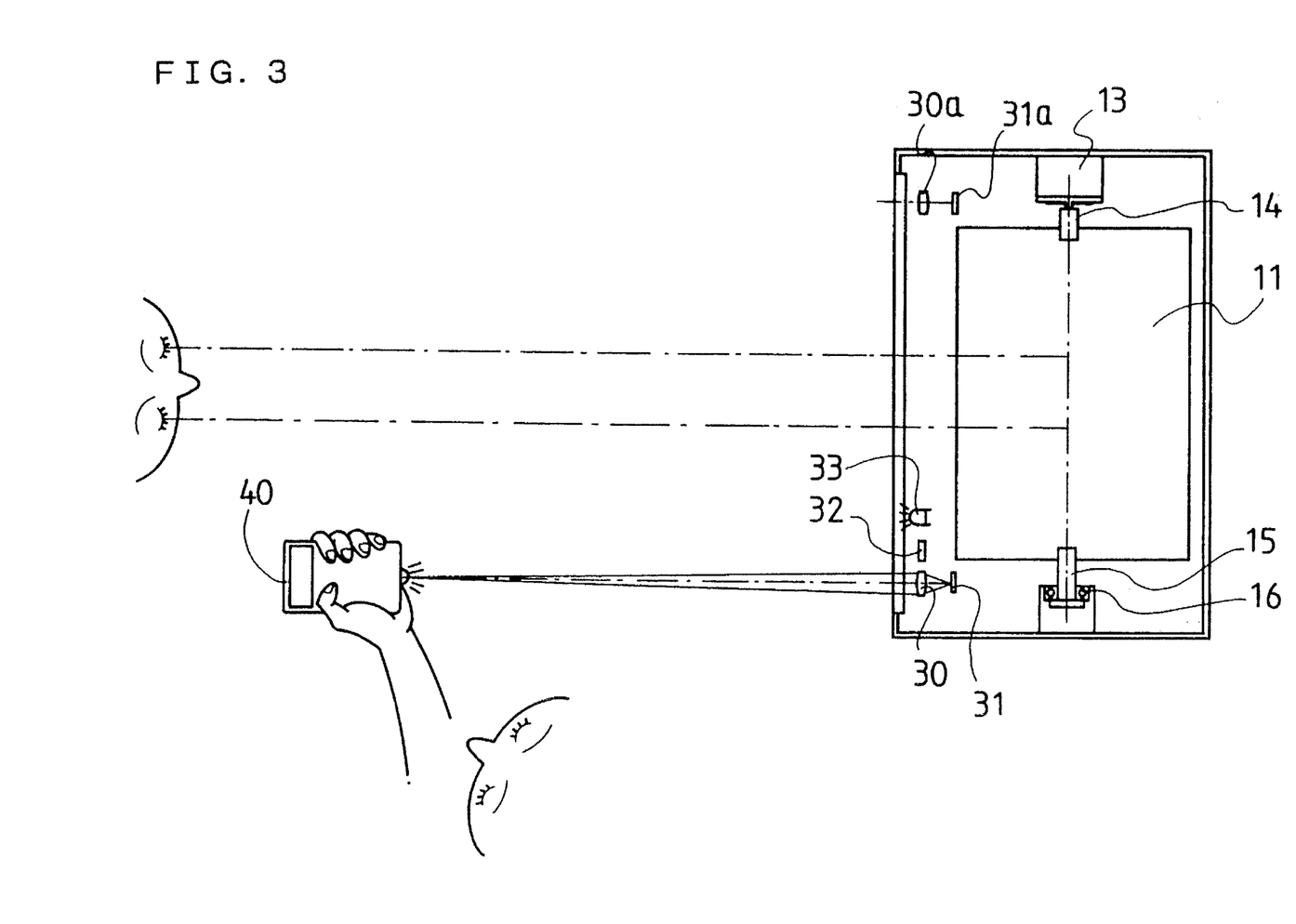
FIG. 3 is a schematic perspective view of the apparatus of the first embodiment, being seen from an upper side thereof.

The examiner puts the rear side of the remote control unit 40 in a predetermined relationship with the examinee's eye as shown in FIG. 3, in other words, places the rear side of the remote control unit 40 in a proper position corresponding to a height of the examinee's eye 1 and outside of a visual line of the examinee's eye by a predetermined distance. It is also possible to put the unit 40 on the visual line of the examinee's eye in the time of positioning in vertical and lateral directions, further to put the same in a rough position in the time of positioning only in a vertical direction, for instance alongside of an ear of the examinee, because the apparatus has relatively large acceptable range in a lateral direction. Then the examiner depresses the button 42 for detecting of the position of the eye 1. The signal of the button 42 is input to the control section 50, and the control section 50 controls the emitting portion 46 to convert the signal into infrared pulse signal. The infrared pulse signal from the emitting portion 46 is received at the light receiving portion 32 of the body 2, is processed at a signal processing circuit 54 with a predetermined process and input to the control section 50. The control section 50 sets position signal of the emitting portion 46 into a receiving state and reads the position of the emitting portion 46 based on the signal of the two-dimensional position detecting element 31. Specifically, the position signal of the element 31 is read in the control section 50 via a signal processing circuit 55, so that data of the position of the examinee's eye in vertical and lateral directions are obtained. The control section 50, based on the data of the position, rotates the motor 13 via the driver 52 and the motor 21 via the driver 53 respectively by a corresponding angle. Accordingly, the angle of the beam splitter 11 with respect to the examinee's eye 1 is changed in accordance with rotation of the motor 13 to adjust the luminous flux in a vertical direction, so that the luminous flux of test chart is directed toward the examinee's eye 1. For orientation in a lateral direction, the body 2 is turned about the axis 24 with respect to the fixed base 20 in accordance with rotation of the motor 21, accordingly, the luminous flux of test chart is directed to the eye 1.

As mentioned above, when the luminous flux comes to be accurately incident into the examinee's eye, the examiner carries out visual acuity test by operation of the remote control unit 40.

When one of the buttons 41 is depressed to select a test chart to be presented, a signal emitted from the emitting portion 46 of the remote control unit 40 is received at the light receiving portion 32 of the body 2. The control section 50 then drives the motor 6 via a driver 56 to arrange on an optical path a test chart corresponding to the signal received at the receiving portion 32 on an optical path. At the same time, the control section 50 transmits information of the test chart being presented from the emitting portion 33 to the remote control unit 40 via a signal processing circuit 57. Based on the signal received at the light receiving portion 47 of the unit 40, test chart information is displayed on the display 45, thereby to prevent difference from occurring between the displayed information and the test chart presented.

Figure 6:
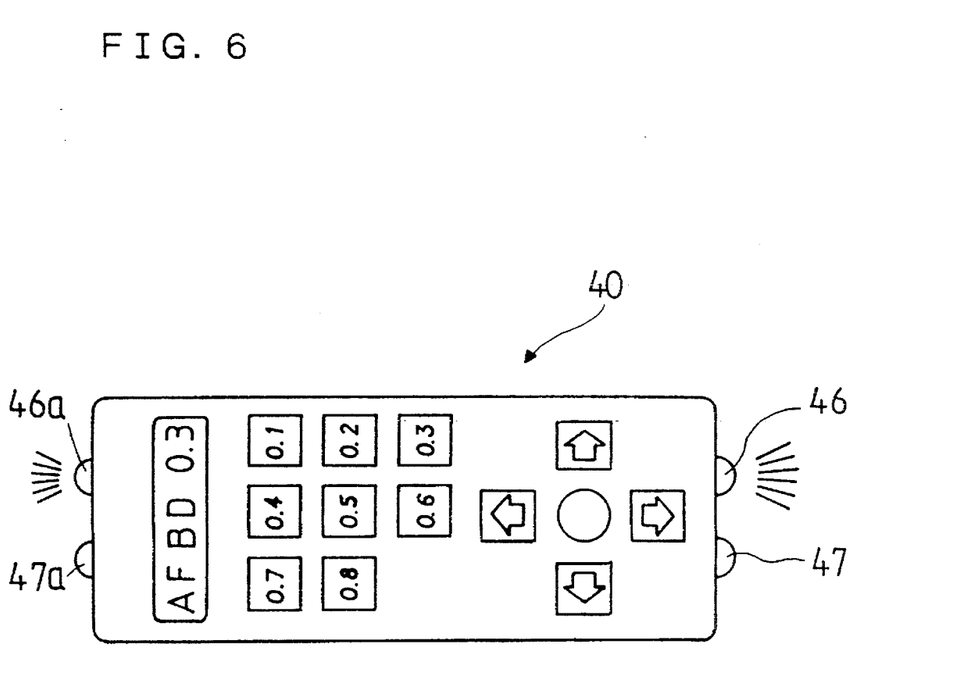
FIG. 6 is a schematic plane view of another remote control unit from the same of FIG. 4.

The emitting portion 46 and the light receiving portion 47 are provided in the rear side of the remote control unit 40 in the above embodiment, because it will be convenient for a case where the examiner places in a position obliquely facing to the examinee. It is further possible to provide in addition another emitting portion 46a and light receiving portion 47a which have the same function as the emitting portion 46 and the light receiving portion 47 respectively, as shown in FIG. 6, at the front side of the remote control unit 40 so that either side of the unit 40 may be put toward the body 2.

Figure 7:
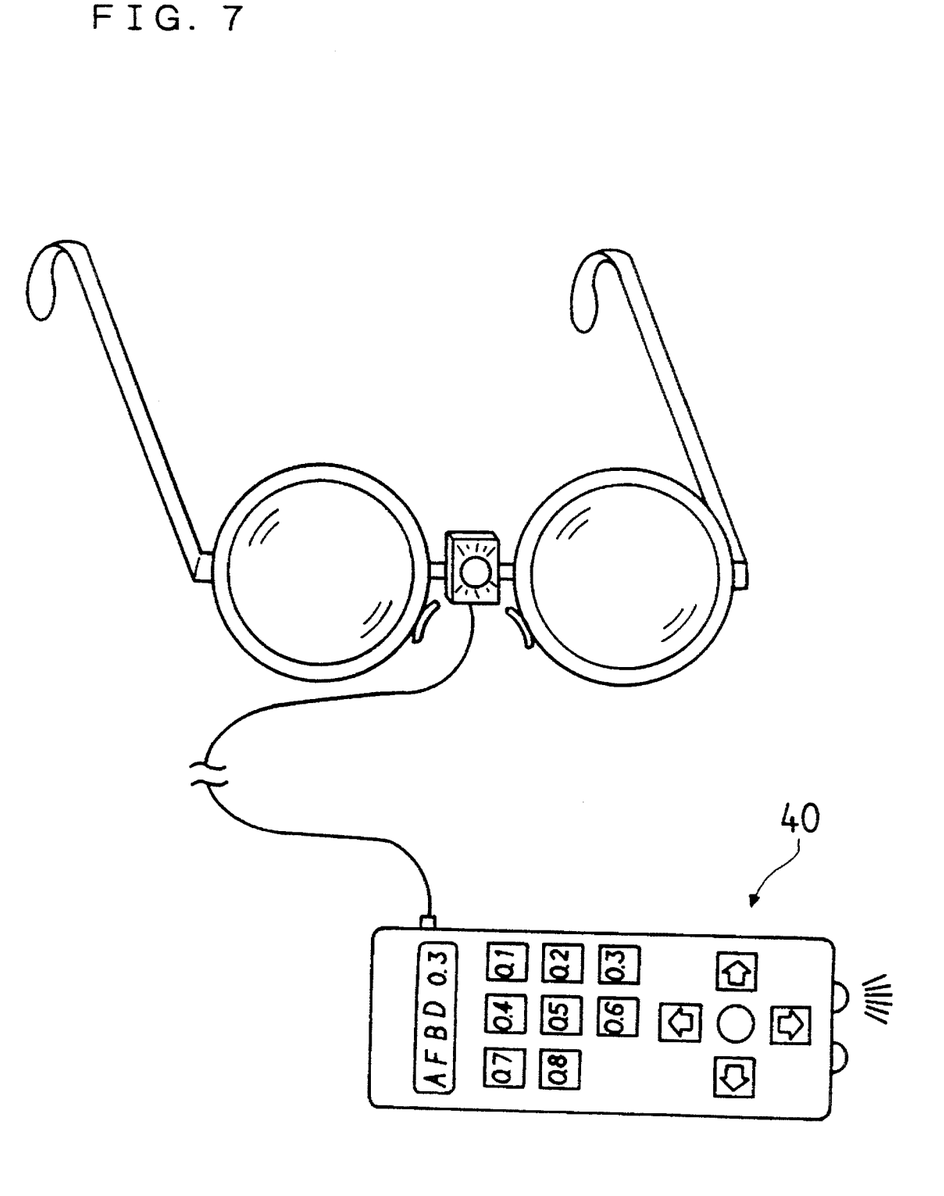
FIG. 7 shows an embodiment wherein a light source for detecting a position of an examinee's eye is attached to spectacles.

In the above embodiment, the light source for detecting of a position of the examinee's eye is provided in the remote control unit, and detecting of the position of the eye is carried out by putting the remote control unit near the eye. The light source may be attached to spectacles or a provisional frame of examination lens which the examinee wears, as shown in FIG. 7.

Although means for adjusting the optical path to a height of the examinee's eye uses changing means of inclination angle of the beam splitter 11 in the first embodiment, it is possible to mount the body 2 on a base movably in a vertical direction, driving this base in accordance with the height position detecting signal.

The above embodiment combines the changing function of the inclination angle of the beam splitter 11 and the function for rotating the upper portion of the body 2 in a horizontal direction, in addition, may construct the beam splitter 11 so as to be rotatable about two axes.

Figure 8:
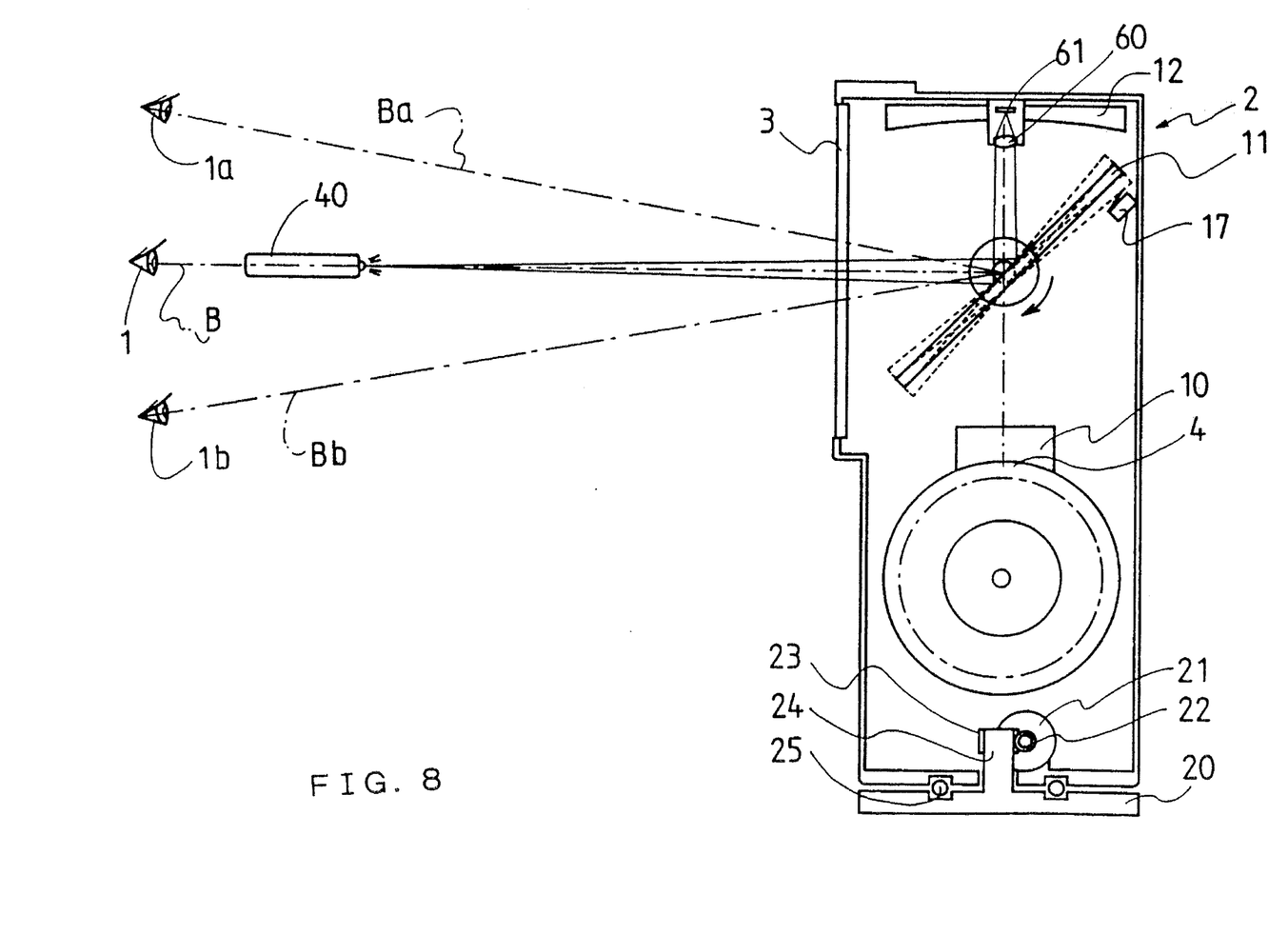
FIG. 8 is a schematic perspective right side view of an apparatus in a second embodiment in accordance with the present invention.
Figure 9:
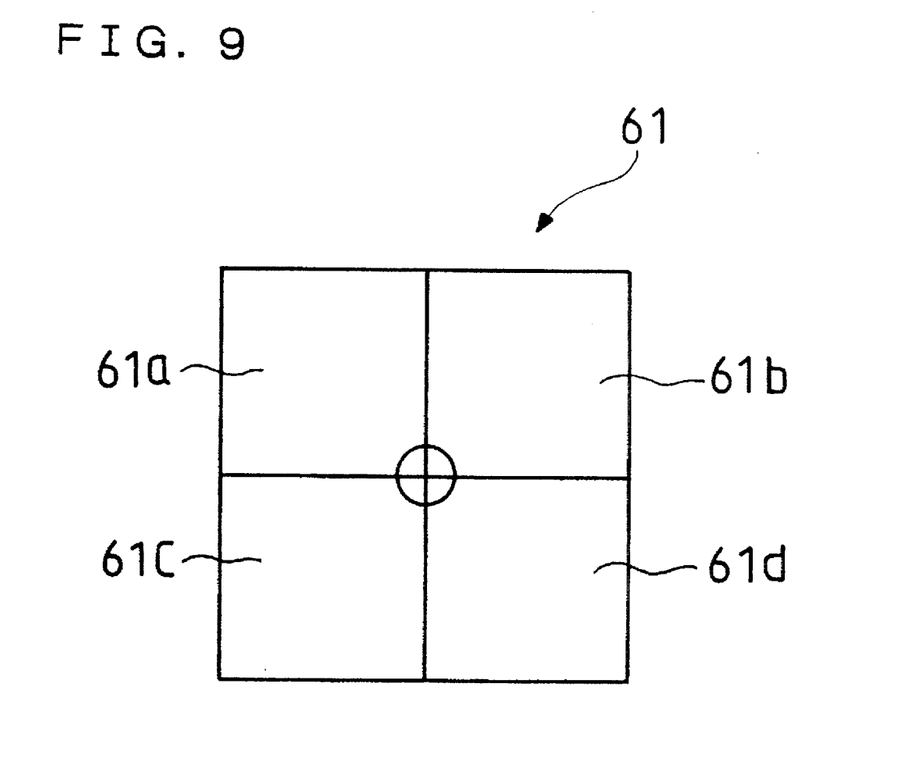
FIG. 9 is a schematic view of a light receiving element divided into four parts.

Next, a second embodiment of the present invention will be described with reference to FIG. 8 which shows a schematic perspective right side view of an apparatus in the second embodiment, wherein similar members as in the first embodiment are labeled the same numbers, similarly in the following embodiments. FIG. 9 shows a four divided light receiving element 61. As shown in FIG. 8, this second embodiment uses a condenser lens 60 and a four divided light receiving element 61 arranged near the concave mirror 12 to detect a position of the examinee's eye, in place of the two-dimensional position detecting element in the first embodiment.

Luminous flux emitted from the emitting portion 48 of the remote control unit 40 is reflected upwardly by the beam splitter 11, falls on the light receiving element 61 divided into four elements 61a–61d via the condenser lens 60 to form an image of the emitting portion 46 thereon. Quantity of light among the four elements 61a–61d of the light receiving element 61 is then compared, the optical path of test chart is changed accordingly. Specifically, the control section 50 compares quantity of light between upper elements (61a, 61b) and lower elements (61c, 61d), for convenience influence of reflection on position is disregarded, and drives the motor 13 to rotate the beam splitter 11 so that the image of the emitting portion shifts to a center in a vertical direction on the light receiving element 61. Similarly, to adjust the optical path of test chart in a lateral direction, the control section 50 compares quantity of light between right elements (61a, 61c) and left elements (61b, 61d) and drives the motor 21 so that the image of the emitting portion 46 shifts to a center in a lateral direction on the light receiving element 61.

As described above, the optical path of test chart is directed to the examinee's eye.

Figure 10:
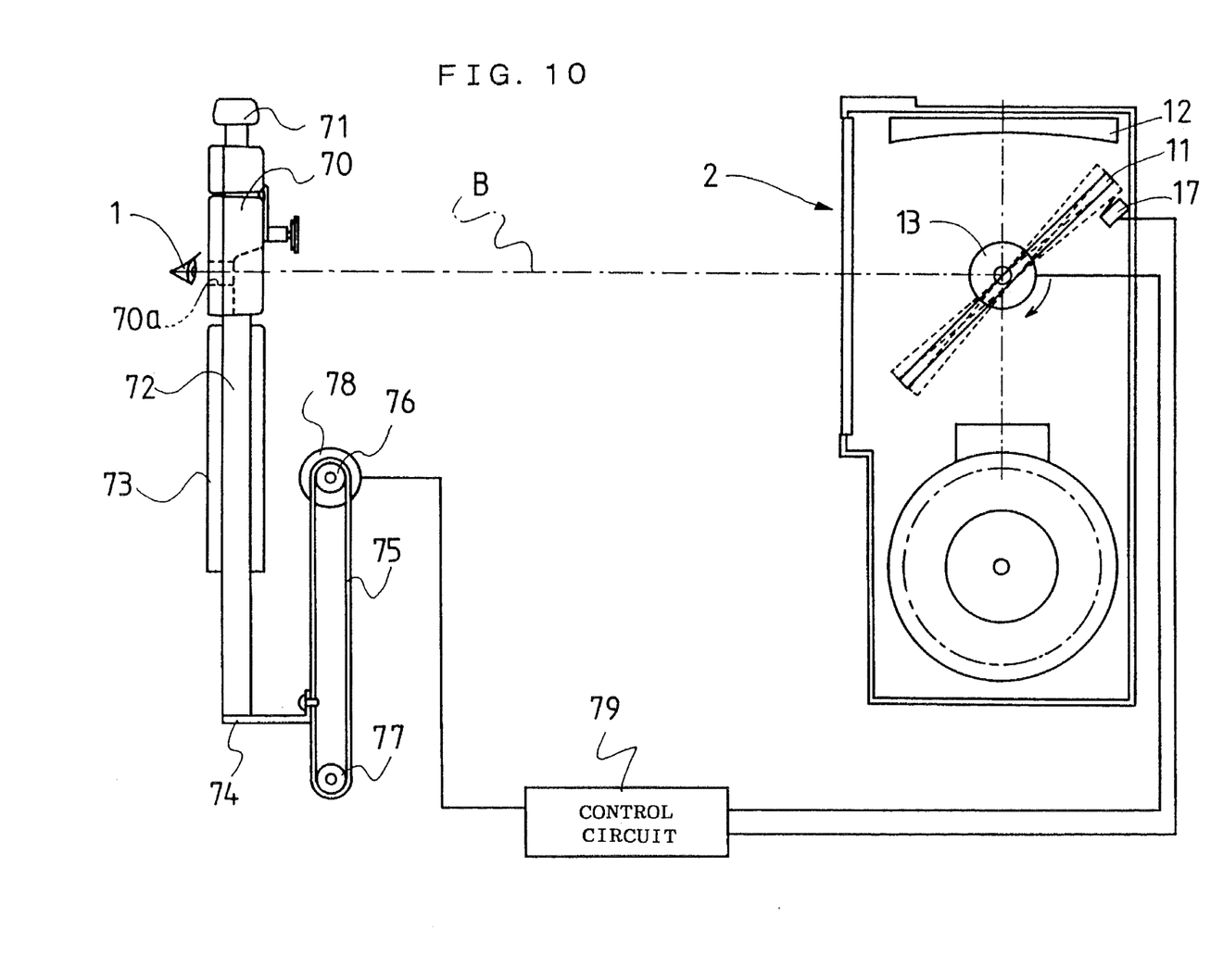
FIG. 10 is a schematic view of an apparatus of a third embodiment in accordance with the present invention.

A third embodiment combines the body 2 for visual acuity test apparatus of the first embodiment with a general subjective refractor, wherein the reflection optical path of the beam splitter 11 is changed based on detecting of the height of the subjective refractor. FIG. 10 shows a schematic perspective view of the apparatus in the third embodiment.

Numeral 70 is the subjective refractor disposed in front of the examinee's eye 1, being suspended from an arm 71 supported by a shaft 72. The shaft 72 is mounted movably in a vertical direction in a pole 73 fixed on a table for eye test not shown in FIG. 10.

The shaft 72 is connected at its lower end with a connecting plate 74 which is horizontally put. Another end of the connecting plate 74 is coupled to a timing belt 75 which is rotated by pulleys 76 and 77 disposed at upper and lower ends of the timing belt 75. In the center of the pulley 76, a rotating axis of a rotary potentiometer 78 is fixed.

Accordingly, when the subjective refractor 70 is moved vertically with the shaft 72 so that the height of a test window 70a of the refractor 70 is adjusted to the height of the examinee's eye 1, a vertical moving position of the shaft 72 is represented by a variation signal of resistance value of the potentiometer 78 and is transmitted to a control circuit 79 via the connecting plate 74 and the timing belt 75. The control circuit 79, receiving the signal, rotates the motor 13 by a predetermined amount (rotating angle) to operate the beam splitter 11, so that the optical path B of test chart is turned toward the examinee's eye 1.

Also in the third embodiment, adjustment of the apparatus in a lateral direction can be carried out as similar as in the first embodiment.

Figure 11:
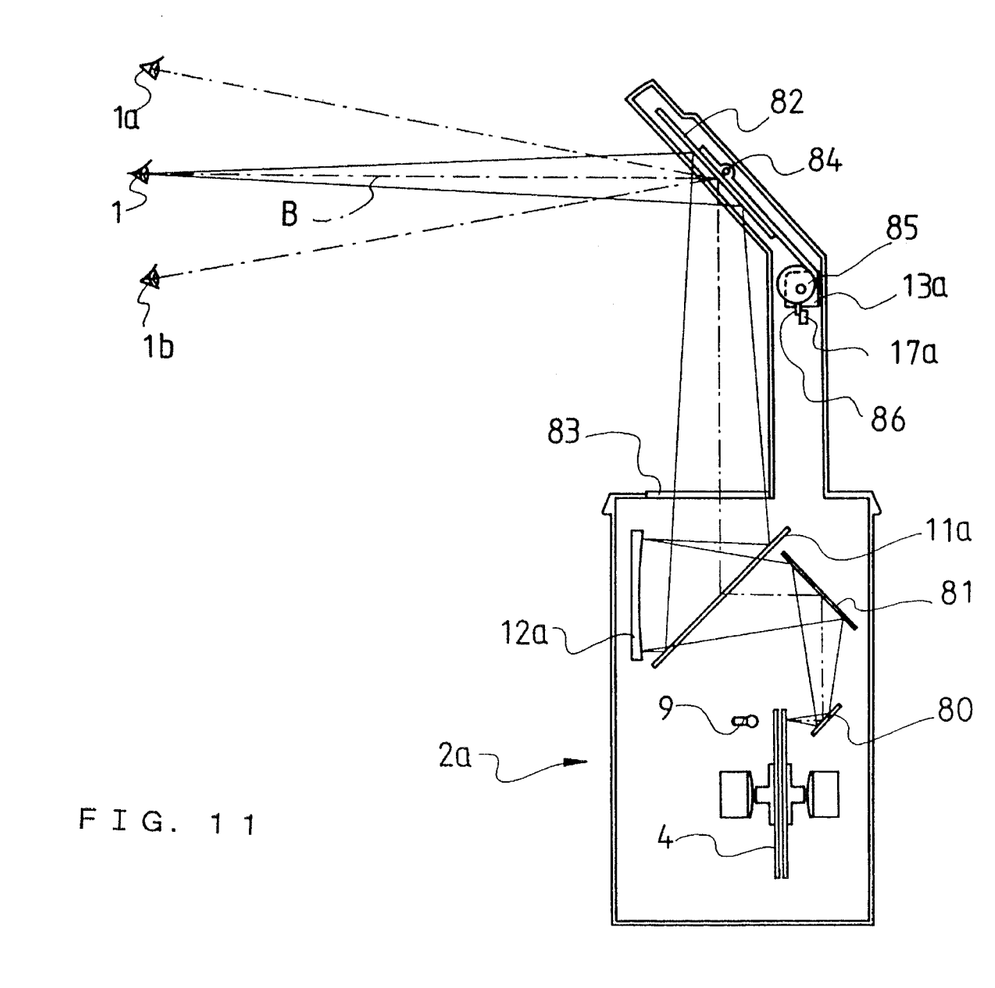
FIG. 11 is a schematic perspective right side view of an apparatus in a fourth embodiment, showing a test chart presenting portion thereof.

A fourth embodiment shows an apparatus which is provided with a test chart displaying system in a different structure from that of the first embodiment. FIG. 11 shows a schematic perspective right side view of the apparatus of the fourth embodiment, particularly showing the displaying system, wherein the same or similar portions or members as in the first embodiment are provided with the same numbers, accordingly omitting repeated explanation herein.

A body 2a of an apparatus for visual acuity test is internally provided with an optical system constructed as the following.

When a part of test charts printed on chart disc plate 4 is illuminated by light of the illumination lamp 9, luminous flux of the test chart illuminated is reflected by a first mirror 80 and a second mirror 81 in turn, is passed through the beam splitter 11a and is delivered to the concave mirror 12a. Then, the luminous flux of test chart, the optical axis of which is made approximately infinit by reflection at the concave mirror 12a, is reflected by the beam splitter 11a upwardly and directed to the examinee's eye 1 via a third mirror 82. A transparent glass 83 is arranged on the optical path between the beam splitter 11a and the third mirror 82 to shut off the interior of the body 2a from the exterior.

The third mirror 82, rotatable about an axis 84, is provided with a cam cylinder 85 at its lower end. To the cam cylinder 85, a rotary shaft of the motor 13a is fixed at a position decentering from the center of the cam cylinder 85. On the peripheral surface of the cam cylinder 85, a rod 86 is fixedly provided and serves to detect an initial position of the third mirror 82 by activating a microswitch 17a when the rotary shaft of the motor 13a is rotated anticlockwise in FIG. 11.

The chart displaying system constructed as above can change inclination angle of the third mirror 82 according to the height of the examinee's eye 1 by controlling the motor 13a based on a signal detecting the height of the eye 1, which is generated from the position detecting means described in the first through third embodiments.

Figure 12:
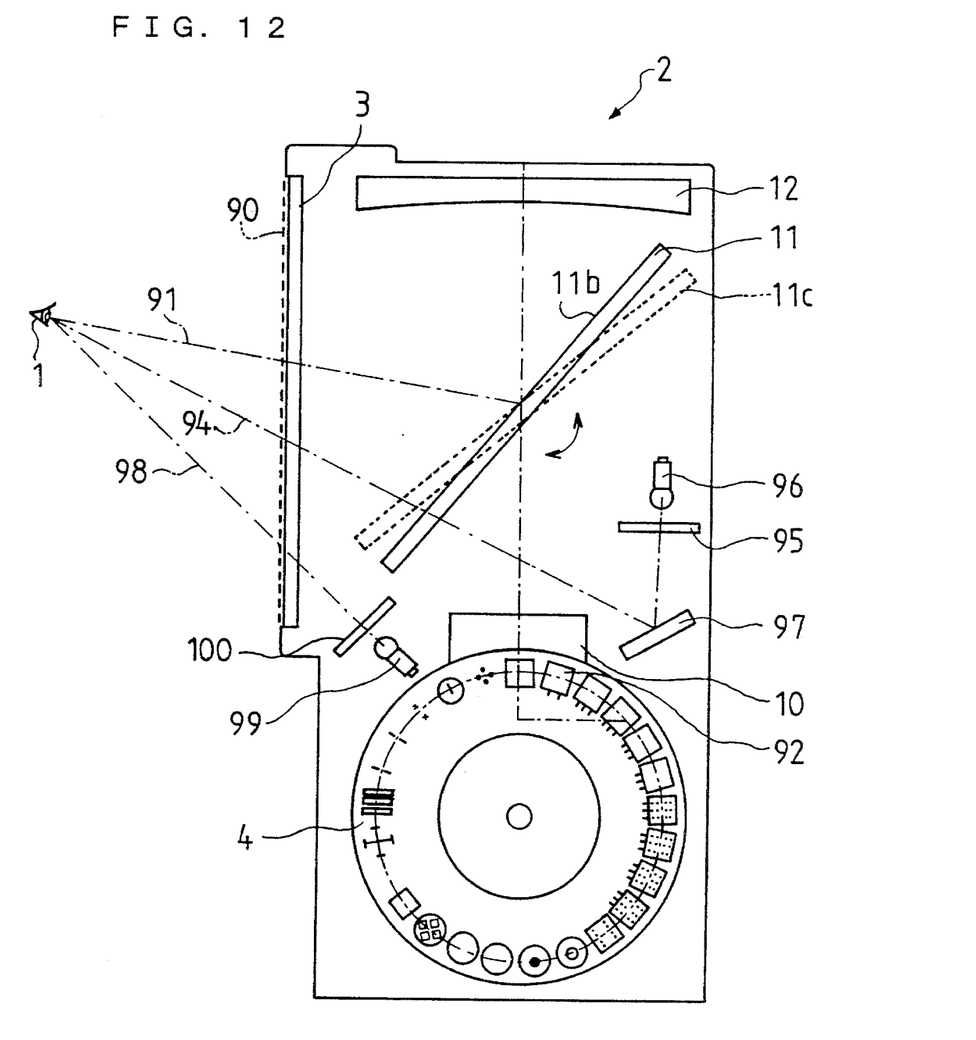
FIG. 12 is a schematic perspective right side view of an apparatus in a fifth embodiment in accordance with the present invention.
Figure 13:
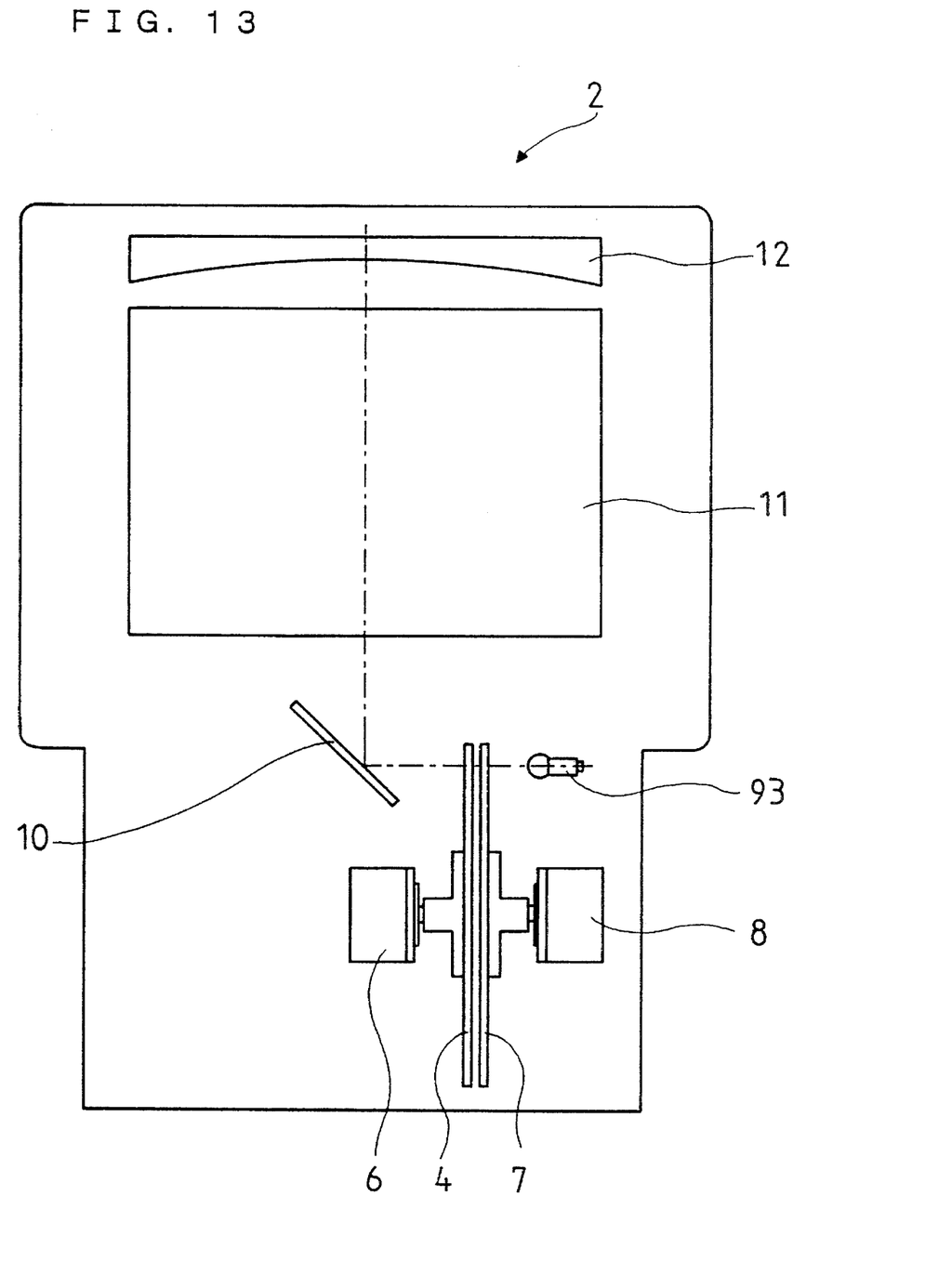
FIG. 13 is a schematic perspective front view of the apparatus in the fifth embodiment.

A fifth embodiment shows an apparatus having a chart displaying system capable of carrying out, with one test window, visual tests needing different test distances. FIG. 12 is a schematic perspective right side view of the apparatus, including an optical system. FIG. 13 shows a schematic perspective front view of the apparatus shown in FIG. 12. In those figures, the same or similar members are labeled the same numbers as in the embodiments described above.

In the body 2 for visual acuity test in the present embodiment, the single window 3 is covered with a semi-transparent filter 90 both surface of which are coated by reflection reducing coating, thereby preventing outside light reflected by the the semi-transparent filter 90 from being incident to the examinee's eye 1. The interior of the body 2 is coated in black color as same as in the aforementioned embodiments.

Numeral 91 is an optical axis along which light of chart for far distance vision test is delivered to the eye 1. On the test chart disc plate 4 made of a glass and the like, test charts 92 for far distance vision test are painted in a circle by chrome evaporation. The disc plate 4 is rotated by the motor 6 to exchangingly present the test chart 92 to be presented. The mask plate 7 having an aperture to present partially test charts for far distance vision test is rotated by the motor 8 to mask test charts needed masking as the disc plate 4 rotates.

Numeral 93 is an illumination lamp for illuminating a test chart 92 for far distance vision test. Luminous flux of the test chart 92 is reflected upwardly by the mirror 10, passed through the beam splitter 11 and reflected by the concave mirror 12. The luminous flux reflected by the concave mirror 12 which optically makes an optical axis of luminous flux approximately infinit is reflected by the beam splitter 11, at its front surface 11b, and is directed to the examinee's eye 1 through the window 3.

The beam splitter 11 is driven by the motor which serves as means for changing inclination angle of the beam splitter, as indicated by a dotted line (11c) shown in FIG. 12, so that the optical axis 91 of far distance vision test chart can be adjusted to the height of the eye 1.

Middle distance vision test system is consisted of an illumination lamp 96, a test chart 95 and a mirror 97. Numeral 94 is an optical axis along which light of test chart for middle distance vision test. Luminous flux of the test chart 95 illuminated by the lamp 96 is reflected by the mirror 97, passed through the beam splitter 11 and the window 3, and reach the examinee's eye 1. Distance between the test chart 95 and the eye 1 is so designed to be about 50 cm in the present embodiment.

Near distance vision test system is consisted of an illumination lamp 99 and a test chart 100 for near distance vision test. Luminous flux of the test chart 100 illuminated by the lamp 99 is transmitted along an optical axis 98 to reach the eye 1 through the window 3. Distance between the test chart 100 for near distance vision test and the eye 1 is so designed to be about 30 cm in the present embodiment.

The optical axis 91 for far distance vision test, the optical axis 94 for middle distance vision test and the optical axis 98 for near distance vision test are arranged respectively so as to pass through a far-section, a near-section and a progressive section of a standard progressive multifocus lens an examinee wearing, so that the examinee can look each test chart for far distance vision test, middle distance vision test, and near distance vision test presented via each optical path through each corresponding section of the lens.

Figure 14:
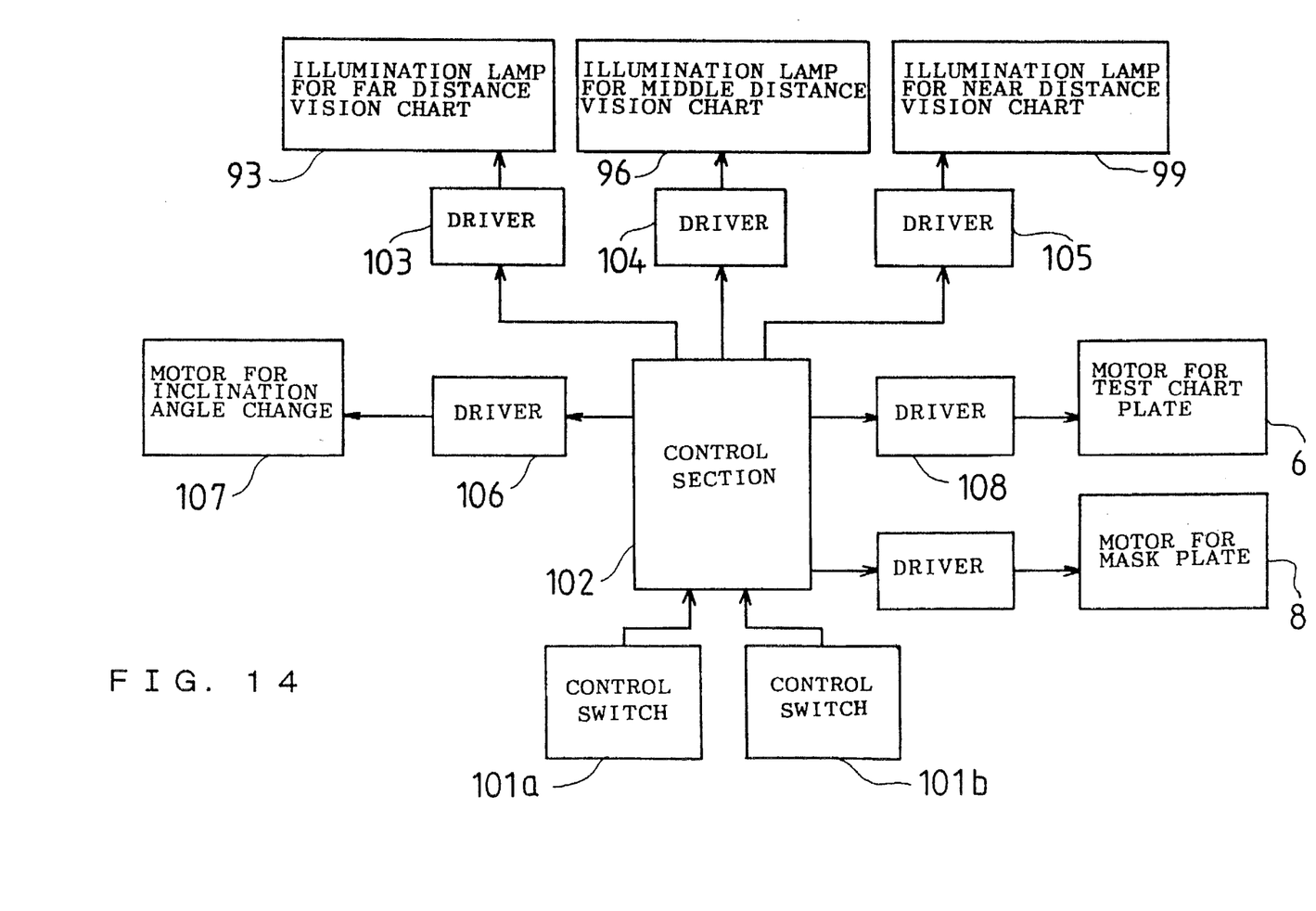
FIG. 14 is a block diagram of an electric system of the apparatus in the fifth embodiment.

Operation of the apparatus constructed above will be described hereinafter with reference to FIG. 14 which shows a block diagram of an electric system of the apparatus. The apparatus in the present embodiment can be served as an apparatus for a single test for far distance vision or near distance vision, but explanation thereof does not described here and special using method of the apparatus will be described hereinafter.

When the examinee is, first, positioned at a predetermined position in front of the apparatus, a progressive mode switch disposed in a control switch 101a is depressed. Control section 102 receiving a signal of the progressive mode switch turns on illumination lamps 93, 96 and 99 simultaneously via drivers 103, 104 and 105 respectively to illuminate each test chart 92, 95 and 100.

Next, an angle changing switch of a control switch 101b put in the examinee's hand is activated and the control section 102 drives a motor 107 for changing inclination angle of the beam splitter 11 via a driver 106. Inclination angle of the beam splitter 11 is adjusted so that the examinee can look the test chart 92 for far distance vision test at a predetermined position (center in the present embodiment) of the beam splitter 11. After the adjustment, a test chart to be presented is selected through operation of selecting buttons provided in the control switch 101a. The control section 102 drives the motor 6 for test chart disc via a driver 108 to set a test chart corresponding to the switch signal input thereto on the optical axis 91 for far distance vision test.

By using the apparatus mentioned above, visual acuity tests needing different test distances can be carried out through a single window.

The foregoing description of the preferred embodiment of the invention has been presented for purposes of illustration and description. It is not intended to be exhaustive or to limit the invention to the precise form disclosed, and modifications and variations are possible in light of the above teachings or may be acquired from practice of the invention. The embodiment chosen and described in order to explain the principles of the invention and its practical application to enable one skilled in the art to utilize the invention in various embodiments and with various modifications as are suited to the particular use contemplated. It is intended that the scope of the invention be defined by the claims appended hereto, and their equivalents.

What is claimed is:

1. An apparatus for visual acuity test of an examinee's eye comprising:

means for changing and presenting test chart to the examinee's eye;

a switch for designating test chart to be presented by said test chart presenting means;

a light delivery optical system for delivering luminous flux of test chart from said test chart presenting means to the examinee's eye, the light delivery optical system comprising a concave mirror for making said luminous flux of test chart optically from 4 m ahead of the examinee to infinite and a first reflection mirror for reflecting the luminous flux reflected said concave mirror to the examinee's eye; and means for adjusting reflection angle of said reflection mirror so as to fit to a height of the examinee's eye;

a housing for internally mounting said test chart presenting means and said light delivery optical system, the housing having an aperture to allow the luminous flux of test chart pass therethrough and the aperture being provided with a filter on which reflection reducing coating is coated.

2. An apparatus for visual acuity test in accordance with claim 1, wherein said test chart presenting means is provided with a test chart disc on which test charts are printed and an illumination lamp for illuminating a test chart disposed at upper position of the test chart disc, the disc surface being arranged parallel to a visual line of the examinee.

3. An apparatus for visual acuity test in accordance with claim 1, wherein said test chart presenting means is provided with a test chart disc on which test charts are printed and an illumination lamp for illuminating a test chart disposed at upper position of the test chart disc, the disc surface being arranged parallel to a visual line of the examinee, said light delivery optical system has a second reflection mirror for reflecting luminous flux of test chart presented by the test chart presenting means toward said concave mirror, and said first mirror is a half mirror.

4. An apparatus for visual acuity test in accordance with claim 1, wherein said test chart presenting means has a plurality of means for presenting test chart, each means having a different test distance from each other.

5. An apparatus for visual acuity test of an examinee's eye comprising:

means for changing and presenting test chart to the examinee's eye;

a switch for designating test chart to be presented by said test chart presenting means;

a light delivery optical system for delivering luminous flux of test chart from said test chart presenting means to the examinee's eye, the light delivery optical system comprising a concave mirror for making said luminous flux of test chart optically from 4 m ahead of the examinee to infinite and a first reflection mirror for reflecting the luminous flux reflected said concave mirror to the examinee's eye;

means for adjusting reflection angle of said first reflection mirror;

means for detecting a height of the examinee's eye; and means for controlling said mirror angle adjusting means based on results detected by said height detecting means.

6. An apparatus for visual acuity test in accordance with claim 5, wherein said height detecting means comprises means for emitting light to indicate a height of the examinee's eye and position detecting optical element for detecting luminous flux of said light emitting means.

7. An apparatus for visual acuity test in accordance with claim 6, wherein said light emitting means is provided in said test chart designating switch, the switch being a portable controller, wherein the controller is put in a predetermined position with respect to the examinee's eye and drives said light emitting means to emit light toward the position detecting optical element.

8. An apparatus for visual acuity test in accordance with claim 7, wherein said controller having means for transmitting optical signal to designate test chart to be presented, said signal transmitting means being used in common as said light emitting means.

9. An apparatus for visual acuity test in accordance with claim 5, wherein said mirror angle adjusting means has a first means for moving luminous flux of test chart in a vertical direction and a second means for moving the same in a lateral direction.

\* \* \* \* \*